(12) United States Patent
Bala et al.

(10) Patent No.: US 10,119,946 B2
(45) Date of Patent: Nov. 6, 2018

(54) STERILIZATION TEST STRIP

(71) Applicant: American Sterilizer Company, Mentor, OH (US)

(72) Inventors: Harry Bala, South Barrington, IL (US); Mark Bala, Chicago, IL (US)

(73) Assignee: AMERICAN STERILIZER COMPANY, Mentor, OH (US)

( * ) Notice: Subject to any disclaimer, the term of this patent is extended or adjusted under 35 U.S.C. 154(b) by 244 days.

(21) Appl. No.: 15/136,006

(22) Filed: Apr. 22, 2016

(65) Prior Publication Data

US 2017/0307573 A1    Oct. 26, 2017

(51) Int. Cl.
*G01K 11/06* (2006.01)
*A61L 2/28* (2006.01)
*G01N 31/22* (2006.01)
*A61L 2/07* (2006.01)

(52) U.S. Cl.
CPC .............. *G01N 31/226* (2013.01); *A61L 2/07* (2013.01); *A61L 2/28* (2013.01); *G01K 11/06* (2013.01)

(58) Field of Classification Search
CPC .. A61L 2/07; A61L 2/28; G01K 11/06; G01K 11/08; G01K 11/12; G01N 31/226
USPC ........ 116/207, 216, 217, 218, 219; 374/106, 374/162
See application file for complete search history.

(56) References Cited

U.S. PATENT DOCUMENTS

| 3,313,266 A | 4/1967 | Kelson |
| 3,341,238 A | 9/1967 | White |
| 3,652,249 A | 3/1972 | White |
| 3,954,011 A * | 5/1976 | Manske .................... G01K 3/04 116/207 |
| 3,981,683 A | 9/1976 | Larsson et al. |
| 4,410,493 A * | 10/1983 | Joslyn .................. G01N 31/226 116/219 |
| 4,448,548 A | 5/1984 | Foley |
| RE36,062 E * | 1/1999 | Speelman et al. ........ A61L 2/28 116/207 |
| 9,623,134 B1 | 4/2017 | Bala |
| 2011/0211991 A1* | 9/2011 | Foltz et al. ............... A61L 2/28 422/28 |
| 2012/0236900 A1* | 9/2012 | Hubbard et al. ......... G01K 3/04 374/102 |
| 2013/0287059 A1* | 10/2013 | Selman et al. ........... G01K 3/04 374/104 |
| 2014/0154150 A1* | 6/2014 | Bala .......................... A61L 2/07 422/402 |
| 2014/0273239 A1* | 9/2014 | Bala .......................... A61L 2/07 436/1 |

(Continued)

FOREIGN PATENT DOCUMENTS

| EP | 0014447 A1 | 8/1980 |
| WO | 0186289 A1 | 11/2001 |

(Continued)

OTHER PUBLICATIONS

International Search Report issued by ISA/EPO in connection with PCT/US2017/028126 dated Feb. 2, 2018.

(Continued)

*Primary Examiner* — R. A. Smith
(74) *Attorney, Agent, or Firm* — Levenfeld Pearlstein, LLC

(57) ABSTRACT

A compact sterilization indicator includes a wicking element having at least two different wicking rates across the length of the wicking element.

16 Claims, 1 Drawing Sheet

(56) References Cited

U.S. PATENT DOCUMENTS

2015/0252403 A1    9/2015  Bala et al.
2015/0253311 A1    9/2015  Bala et al.
2016/0022853 A1*   1/2016  Hajime et al. ............ A61L 2/07
                                                        206/370

FOREIGN PATENT DOCUMENTS

WO    2009091673 A1    7/2009
WO    20170112562 A1   6/2017

OTHER PUBLICATIONS

Written Opinion of the International Searching Authority issued by ISA/EPO in connection with PCT/US2017/028126 dated Feb. 2, 2018.

* cited by examiner

STERILIZATION TEST STRIP

BACKGROUND OF THE INVENTION

It is well known that heat destroys microorganisms. The presence of moisture accelerates this destruction by denaturing or coagulation of the proteins making up the microorganisms. Most microorganisms contain sufficient water so that moderate heat alone, e.g. 80° C.-100° C., will destroy the microorganism. Many bacterial spores, on the other hand, contain substantially no water and require elevated temperatures, in excess of 150° C., for their destruction where dry heat is used. Hence, the destruction of such organisms is generally carried out in the presence of steam in autoclaves.

Such steam sterilization is generally carried out at temperatures of about 250° F. (121° C.) for at least 12 to 15 minutes or for shorter times at higher temperatures e.g. 270° F. (132° C.). Often, to ensure a sufficient safety margin, times as long as 30 minutes are used. Such long sterilization times give the operator a greater degree of confidence that steam has penetrated throughout the autoclave and among all of its contents. However, such long heat cycles are disadvantageous from the standpoint of economy of time, energy consumption, and severe shortening of the useful life of certain types of sterilized material, e.g., fabric gowns, drapes, and the like.

From time to time attempts have been made to develop sterilization indicators which permit quality control of sterilization with the confidence that all microorganisms have been destroyed. One presently used method is through the use of spore strips or samples. Spores that are particularly difficult to destroy are selected as the control standard, e.g., *Bacillus Subtilis* var. *Niger* and *Bacillus Stearothermophilus*. The spore strip or sample is placed in an autoclave with the materials to be sterilized. At the end of the sterilization cycle, the spore strip or sample is studied to determine whether it is possible to grow organisms in a suitable culture medium. Failure of the spores to reproduce indicates death of spores, and hence, adequate sterilization.

Although this control technique is accurate, it suffers from several inherent disadvantages: (1) excessive cost; (2) delay between processing and control data; (3) batch to batch variation of the spores; and (4) heat resistance of spores decreases with storage time.

Several attempts have been made to devise chemical type sterility indicators. One such product is known as Temp-Tube, and is disclosed in, for example, Kelson, U.S. Pat. No. 3,313,266, White, U.S. Pat. No. 3,341,238, and White, U.S. Pat. No. 3,652,249. The device consists of a sealed tube containing a compound with a melting point which corresponds to the sterilization temperature. The device is capable of indicating whether or not the autoclave was held at a temperature above or below the melting point for a period of time once the melting point is reached.

Other sterility indicators are known. One such indicator is disclosed in Larsson, U.S. Pat. No. 3,981,683, and uses a backing strip of aluminum foil having an organic compound containing oxygen or nitrogen in contact with a wicking strip, and a cover strip overlying the organic compound and the wicking strip. The cover strip is a polymeric rate controlling film that permits water vapor to pass through at a rate sufficient to make the strip operable at a temperature to be monitored.

One drawback to the device in Larsson is that the temperature and time parameters at which the indictor indicates an acceptable level of sterilization (e.g., that the temperature has been held at a minimum value for a specified period of time) is not well controlled. As such, the indicator can indicate that the requisite level of sterilization has occurred when in fact is has not.

Another such indicator is disclosed in Foley, U.S. Pat. No. 4,448,548. The device in Foley is directed to a steam sterilization indicator in which a fusible material, in tablet form, is deposited in an embossment in an aluminum backing. A wicking strip is attached to the backing in close proximity to the fusible tablet. A clear plastic material covers the tablet and the strip and is adhered to the backing.

The melting point of the fusible tablet is depressed in the presence of saturated steam. Upon melt, the material in the tablet is absorbed by the wicking strip, producing a color front to provide an indication of the integration of time and temperature in the presence of steam. Various amounts of a binder are used in the tablet to provide a device which may be adjusted to reflect the thermal death curves of various types of microorganisms. The cover and the wick are bonded to the backing by an acrylic adhesive which also affects the rate of the indicator.

As with the Larsson device, a drawback to the device in Foley is that the temperature and time parameters at which the indictor indicates an acceptable level of sterilization is not well controlled and as such, the indicator can indicate that the requisite level of sterilization has occurred when in fact it has not.

Further, U.S. patent application Ser. No. 14/197,932, which is assigned to the Applicant of the present application and incorporated herein by reference, discloses a sterilization test strip that, in a sense, mimic spore kill, and includes two pass zones configured to work for two different sterilization conditions.

A new sterilization test strip is used for each sterilization cycle. Thus, there is a need for cost effective sterilization test strips that can indicate proper sterilization with a margin of safety.

BRIEF SUMMARY OF THE INVENTION

A compact sterilization indicator having a reduced strip length is provided according to various embodiments of the present embodiment.

In one aspect, a sterilization indicator may include a base element, a first adhesive, an indicator chemical composition, a wicking element, a film layer, a paper layer, second adhesive layer, a window defined in the paper layer and the second adhesive layer, and an acceptance marker. The base element may be formed from a thermally conductive material having a length and a width, and may have a recess formed therein extending along about a longitudinal centerline thereof. The recess may be formed within the base material less than the length and the width of the base material. The first adhesive layer may be disposed on the base element, and the indicator chemical composition may be deposited in the recess. The wicking element may be positioned at least in part in contact with the indicator chemical composition and at least in part within the recess. Further, the wicking element may extend less than the length and width of the base element, in which the wicking element may have at least two different wicking rates across the length of the wicking element. The film layer may be positioned over the base element, the wicking element and the indicator chemical composition, and the paper layer may be disposed over the film layer. Further the second adhesive layer may be disposed between the paper layer and the film layer. The indicator may be configured to indicate that an acceptable level of sterilization has occurred when the indicator chemical composition wicks along the wicking element to a location beyond the acceptance marker after a sterilization process.

In an embodiment, the wicking element includes at least two zones, in which a wicking rate of one of the zones may be greater than a wicking rate of another one of the zones. For example, the wicking element may include a first zone, a second zone, and a third zone, in which a width of the first zone is less than a width of the third zone. The second zone, which is arranged between the first zone and the second zone, may have a width that increases from the width of the first zone to the width of the second zone. In such an embodiment, a wicking rate across the first zone may be greater than a wicking rate across the third zone.

In an embodiment, the base element may have a length of about 1.75 inches to about 4 inches, and the wicking element may have a length of about 1.125 inches to about 1.625 inches, in which the first zone may have a width of about 0.125 inches to about 0.375 inches and the third zone may have a width of about 0.175 inches to about 0.425 inches. The width of the first zone may be about 0.03 inches to about 0.07 inches less than the width of the third zone. In such an embodiment, the sterilization indicator may be configured to work for sterilization process criteria selected from 12 minutes at 121° C., 15 minutes at 121° C., 20 minutes at 121° C., 30 minutes at 121° C., 4 minutes at 132° C., 3.5 minutes at 134° C., 4 minutes at 134° C., 5 minutes at 134° C., 7 minutes at 134° C., and 3 minutes at 135° C.

In some embodiments, the sterilization indicator may be configured for steam sterilization processes, and include an indicator chemical composition containing a temperature and steam sensitive material. The indicator chemical composition may also contain a dye. Further, the film layer may be formed from a cast polypropylene having a thickness of about 2.0 to 2.2 mils or about 3.0 to 3.2 mils. The base element may be formed from an aluminum foil, such as an aluminum foil having a thickness of about 3 mils. Further, the first adhesive layer may be formed from an acrylic adhesive. The second adhesive layer may also be formed from an acrylic adhesive. The wicking element may be formed from a wicking paper having a basis weight of about 66 $g/m^2$ to about 186 $g/m^2$ and a thickness of about 7.3 mil to about 13.3 mil.

In an embodiment, the wicking element may include at least two zones comprising a first zone and a second zone, in which the first zone has a thickness greater than the second zone. In such an embodiment, the wicking element may be formed from a first layer of a wicking paper and the first zone may include a second layer of a wicking material, in which the second layer may be formed from the same wicking paper or a different wicking paper than the first layer.

In another embodiment, the wicking element may include at least two zones comprising a first zone and a second zone, in which the first zone is formed from a first wicking paper and the second zone is formed from a second wicking paper, wherein the first wicking paper has a wicking rate greater than that of the second wicking paper.

In another aspect, a sterilization indicator including a base element, a first adhesive, an indicator chemical composition, a wicking element having at least two different widths across a length of the wicking element, a film layer, a paper layer, second adhesive layer, a window defined in the paper layer and the second adhesive layer, and an acceptance marker is provided.

In an embodiment, the sterilization indicator may be configured to indicate an acceptable level of steam sterilization. In such an embodiment, the wicking element may include a first zone, a second zone, and a third zone, in which a width of the first zone is less than a width of the third zone, and the second zone is arranged between the first zone and has a width that increases from the width of the first zone to the width of the second zone. Further, the wicking element may be positioned such that an end portion of the first zone is in contact with the indicator chemical composition.

The sterilization indicator may be configured to work for steam sterilization criteria selected from 12 minutes at 121° C., 15 minutes at 121° C., 20 minutes at 121° C., 30 minutes at 121° C., 4 minutes at 132° C., 3.5 minutes at 134° C., 4 minutes at 134° C., 5 minutes at 134° C., 7 minutes at 134° C., and 3 minutes at 135° C. The base element may have a length of about 1.75 inches to about 4 inches, and the wicking element may have a length of about 1.125 inches to about 1.625 inches, in which the first zone has a width of about 0.125 inches to about 0.375 inches and the third zone has a width of about 0.175 inches to about 0.425 inches. The width of the first zone may be about 0.03 inches to about 0.07 inches less than the width of the third zone.

In such an embodiment, the indicator chemical composition may contain a temperature and steam sensitive material, and the film layer may be formed from a cast polypropylene having a thickness of about 2.0 to 2.2 mils or about 3.0 to 3.2 mils, and the wicking element may be formed from a cotton wicking material having a basis weight of about 186 $g/m^2$ and a thickness of about 13.3 mil.

These and other features and advantages of the present indicator will be apparent from the following detailed description, in conjunction with the appended claims.

BRIEF DESCRIPTION OF THE SEVERAL VIEWS OF THE DRAWINGS

The benefits and advantages of the present device will become more readily apparent to those of ordinary skill in the relevant art after reviewing the following detailed description and accompanying drawings, wherein.

DETAILED DESCRIPTION OF THE INVENTION

Figure 1:
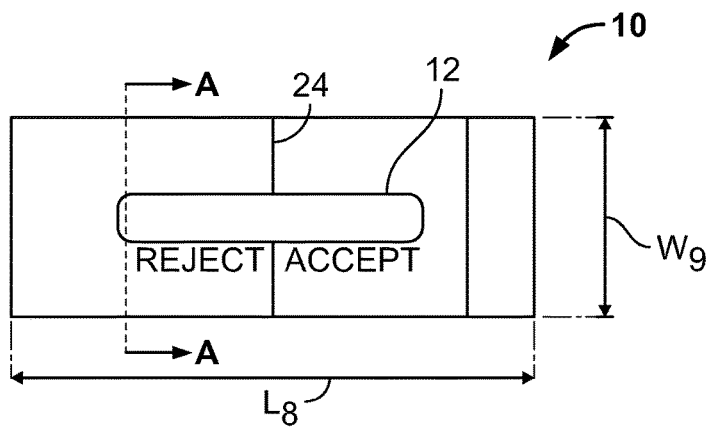
FIG. 1 is a top plan view of a sterilization indicator according to an embodiment.

While the present device is susceptible of embodiment in various forms, there is shown in the drawings and will hereinafter be described a presently preferred embodiment with the understanding that the present disclosure is to be considered an exemplification of the device and is not intended to be limited to the specific embodiments illustrated.

Figure 2:
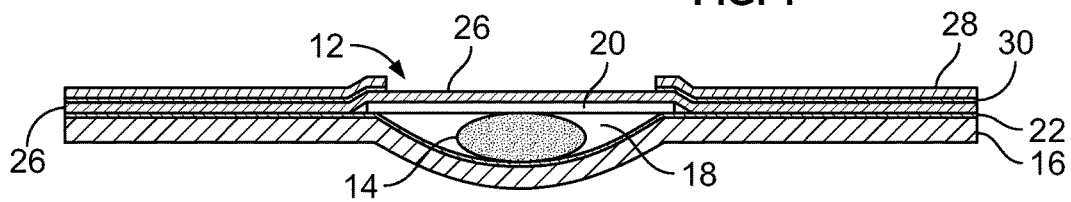
FIG. 2 is a cross-sectional view taken along line A-A of FIG. 1.

Referring to FIGS. 1 and 2, an embodiment of a sterilization indicator 10 is shown. The sterilization indicator 10 may have an open window 12 through which the wicking of an indicator chemical composition 14 may be observed to determine whether an acceptable level of sterilization has occurred. FIG. 2 is a cross-sectional illustration of the sterilization indicator 10 of FIG. 1. The sterilization indicator 10 generally includes a base element 16, a first adhesive layer 22, a wicking element 20, a film layer 26, a second adhesive layer 30, a paper layer 28, and an indicator chemical composition 14. The sterilization indicator 10 may also include a marker 24 for marking an acceptance area. Further, the wicking element 20 may be configured have at least two different widths $W_{38}$, $W_{40}$ along the length $L_{31}$ of the wicking element 20 as will be discussed in more detail below.

In some embodiments, the sterilization indicator 10 may be configured as a single use type 5 indicator as classified by ANSFAAMI/ISO 11140-1:2014 or Class 5 indicator as classified by ANSI/AAMI/ISO 11140-1:2005. The sterilization indicator 10 for type 5 or Class 5 may be configured to integrate three criteria for proper steam sterilization, namely, time, temperature, and steam. When processed in a sterilization cycle with a load, the sterilization indicator 10 may indicate, with a margin of safety, whether the proper steam sterilization criteria have been achieved.

A sterilization indicator 10 for type 5 or Class 5 may comprise a base element 16 formed from an aluminum foil and a first adhesive layer 22 coated thereon. An embossed cavity or recess 18 may be formed proximate one end of the base element 16, which may be filled with a steam sensitive chemical composition 14. The chemical composition 14 may have a melting point that can be depressed by steam, such that the dry heat melting point of the chemical composition 14 is higher than a steam sterilization temperature. A wicking element 20 having at least two different widths along its length may be arranged on the first adhesive layer 22, such that one end of the wicking element 20 is in contact with the chemical composition 14. Further, a film layer 26 formed from a steam sensitive polymeric material may be laminated with a paper layer 28 via a second adhesive 30 therebetween, and disposed as a continuous layer covering substantially the entire top surface of the base element 16, such that the film layer 26 is attached to the base element 16 by the first adhesive layer 22 and the chemical composition 14 and the wicking element 20 are sealed between the film layer 14 and the base element 16. The window 12 may be provided on the paper layer 28 as a cut out area, such that the window 12 overlies the wicking element 20 and the wicking of the chemical composition 14 may be visible to a user.

During a sterilization process, steam may penetrate the film layer 26 and lower the melting point of the chemical composition 14. As such, the rate at which the chemical composition 14 melts may be affected by the vapor transmission rate of the film layer 26 and the sterilization temperature. As the chemical composition 14 melts and liquefies in heat and steam, and the liquefied chemical composition 14 may be absorbed by the wicking element 20 and wick across the length of the wicking element 20 with time. The chemical composition 14 may contain a dye, such that the wicking of the liquefied chemical composition 14 may be visible through the widow 12.

An acceptable sterilization process cycle may be indicated when the liquefied chemical composition 14 wicks across the wicking element 20 to a point beyond a marker 24 within an acceptance area of the sterilization indicator 10. Thus, if the chemical composition 14 melts and wicks prematurely before all criteria of sterilization have been satisfied, a false sterilization acceptance may result, which may have dire consequences. Further, characteristics and properties of each component of the sterilization indicator 10 may affect the melting and wicking rate of the chemical composition 14.

Thus, careful selection and configuration of each component is critical in providing a sterilization indicator that can indicate whether proper sterilization criteria have been achieved with a margin of safety. During an extensive research and development of a cost effective compact size sterilization indicator, it was discovered that the wicking element 20 may be specifically configured for a compact size sterilization indicator, which may work as a type 5 indicator or a Class 5 indicator or as other type indicators, such as a type 4 indicator.

Variables affecting a wicking rate of the wicking element 20 may include the type of wicking material, a thickness of a wicking material, and dimensions of the wicking element. The wicking element 20 may be formed from a suitable wicking material. In some embodiments, the wicking element 20 may be formed from a wicking paper having a basis weight of about 66 grams per square meter ($g/m^2$) to about 186 $g/m^2$, and a caliper or thickness of about 7.5 thousandths of an inch (mil) to about 13.3 mil. For example, the wicking element 20 may be formed from a low-ash, qualitative paper having a basis weight of about 66 $g/m^2$ and a thickness of about 7.3 mil, or a low-ash, qualitative paper having a basis weight of about 87.7 $g/m^2$ and a thickness of about 7.5 mil, or from a white, smooth surface, cotton paper having a basis weight of about 186 $g/m^2$ and a thickness of about 13.3 mils.

Further, the wicking element 20 may be configured to have at least two different wicking rates along the length of the wicking element 20. For example, the wicking element 20 may be configured to include multiple zones, each of which having a different wicking rate.

Figure 3:
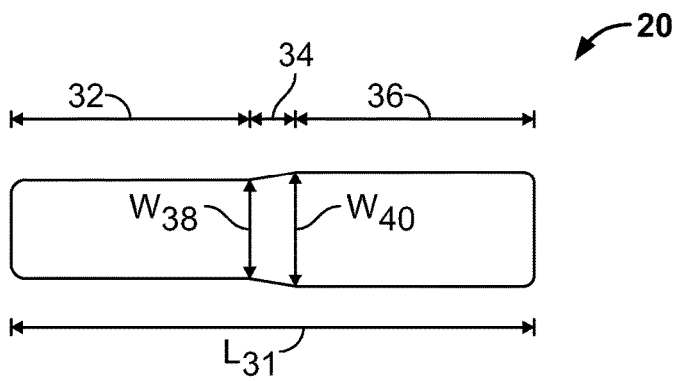
FIG. 3 is a top plan view of a wicking element according to an embodiment.
Figure 4:
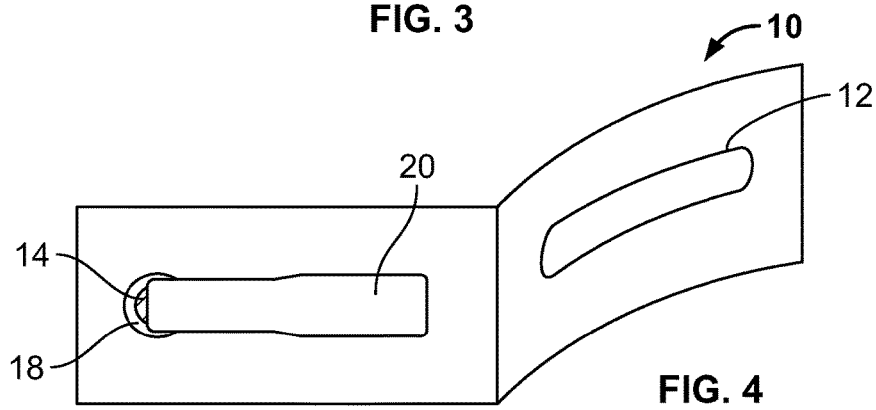
FIG. 4 is a top perspective view of the sterilization indicator of FIG. 1 with a paper layer, a second adhesive layer, and a film layer peeled off.

In the embodiment shown in FIGS. 3 and 4, the wicking element 20 includes a first zone 32, a second zone 34, and a third zone 36, in which a width $W_{38}$ of the first zone 32 is less than a width $W_{40}$ of the third zone 36. The second zone 34 may have a gradually increasing width from the width $W_{38}$ to width $W_{40}$. In such an embodiment, the liquefied chemical composition 14 may wick across each zone at a different wicking rate, in which the third zone 36 provides the most resistance to wicking to slow down the wicking rate.

The sterilization indicator 10 may be configured as a compact sterilization indicator strip having a length $L_8$ of about 1.5 inches to about 4 inches, preferably about 1.75 inches to about 2.5 inches, more preferably about 2 inches, and a width $W_9$ of about 0.5 inches to about 1 inch, preferably about 0.75 inches. The wicking element 20 may be configured according to the size of the sterilization indicator 10 and sterilization criteria.

In an embodiment, the wicking element 20 may be formed from a white, smooth surface, cotton paper having a basis weight of about 186 $g/m^2$ and a thickness of about 13.3 mils. The wicking element 20 may have a length $L_{31}$ of about 0.875 inches to about 1.875 inches, preferably about 1.125 inches to about 1.625 inches, more preferably about 1.375 inches, and may include three zones 32, 34, 36, in which a width $W_{38}$ of the first zone 32 may be less than a width $W_{40}$ of the third zone 36. The second zone 34 may have a gradually increasing width or taper. Accordingly, the liquefied chemical composition 14 may move along each zone at different wicking rates, wherein a wicking rate across the first zone 32 (the narrowest portion of the wicking element 20) is greater than a wicking rate of the third zone 36 (the widest portion of the wicking element 20.)

As shown in FIGS. 2-4, the wicking element 20 is configured smaller than the base element 16, such that the wicking element 20 may be generally centered on the base element 16 with an end portion of the first zone 32 in contact with the chemical composition 14. FIG. 4 is a perspective top view of the sterilization indicator 10 with the film layer 26, the second adhesive layer 30, and the paper layer 28 peeled away. As shown, the wicking element 20 may extend longitudinally along the base element 16, such that at least some portion of the wicking element 20 is securely attached to the base element 20 by the first adhesive layer 22. In this manner, the indicator chemical composition 14 and the wicking element 20 are bounded within the four sides of the sterilization indicator 10.

The first zone 32 may have a width of about 0.125 inches to about 0.375 inches, preferably about 0.25 inches, and a length of about 0.5 inches to about 0.750 inches, preferably about 0.625 inches. The third zone 36 may have a width of about 0.175 inches to about 0.425 inches, preferably about 0.30 inches, and a length of about 0.5 inches to about 0.750 inches, preferably about 0.625 inches. The second zone 34 may have a length less than about 0.25 inches, preferably about 0.125 inches, and a width that gradually increases from the width of the first zone 32 to the width of the third zone 36.

In another embodiment, the wicking element may be configured to include at least two zones, in which at least one of the zones has a thickness different than a thickness of another zone to provide at least two different wicking rates. In such an embodiment, the width of the wicking element may remain constant throughout the length of the wicking element, while a thickness of the wicking element in one of the zones may be thicker or thinner than another zone. For example, the wicking element may include two zones, in which the wicking element is formed from a layer of a suitable first wicking material and one of the two zones includes an additional layer of a wicking material formed from the same or a different wicking material than the first wicking material. In another example, the wicking element may include two zones, in which a first zone is formed from a first wicking material and a second zone is formed from a second wicking material, wherein a thickness of the first wicking material is greater than that of the second wicking material.

In another embodiment, the wicking element may be configured to include at least two zones, in which at least one of the zones is formed from a first wicking material and another zone is formed from a second wicking material, wherein the first wicking material has a wicking rate greater than that of the second wicking material. In such an embodiment, the thickness and the width of the wicking element may remain constant throughout the length of the wicking element.

In yet another embodiment, the wicking element may be configured to include at least two zones, in which one of the zones may have a thickness different than a thickness of another zone and/or a width different than a width of another zone and/or may be formed from a wicking material having a wicking rate different than that of another zone.

The indicator chemical composition 14 may be formed from a steam and temperature sensitive chemical composition. The indicator chemical composition may also contain a colorant in a concentration of about 0.01 percent by weight.

A film layer 26 may be applied over the base element 16, indicator chemical composition 14, and wicking element 20, and may be adhered to the base element 16 by the first adhesive layer 22. The film layer 26 may be formed from a suitable steam sensitive transparent film. The paper layer 28 and the second adhesive layer 30 may be disposed over the film layer 26. The paper layer 28 and adhesive layer 30 may include the window 12 that is cut out (as seen in FIG. 1) to allow for visual inspection within the window 12, through the film layer 26.

In an embodiment, the base element 16 may be formed from an aluminum foil, and a layer of an acrylic adhesive may be coated on the base element 16 to form the first adhesive layer 22. In some embodiments, a foil adhesive label having a 3/1000 inch (3 mil) thickness may be used to form the base element 16 and the first adhesive layer 22. Further, an adhesive coated paper may be used to form the paper layer 28 and the second adhesive layer 30. For example, an acrylic adhesive coated paper may be used to form the paper layer 28 and the second adhesive layer 30. The film layer 26 may be formed from a cast polypropylene film having a thickness of about 2.0 to 2.2 mil or 3.0 to 3.2 mil.

The sterilization indicator 10 may be configured to work for steam sterilization processes at about 115° C. to about 138° C., such as gravity, flash and pre vacuum sterilization cycles. For example, the sterilization indicator 10 may be configured for steam sterilization cycles for 12 minutes at 121° C., 15 minutes at 121° C., 20 minutes at 121° C., 30 minutes at 121° C., and 4 minutes at 132° C., 3.5 minutes at 134° C., 4 minutes at 134° C., 5 minutes at 134° C., 7 minutes at 134° C., and 3 minutes at 135° C. The wicking element 20 may be configured for particular sterilization criteria. The location of the marker 24 may also be adjusted according to the sterilization criteria.

In an embodiment, the sterilization indicator 10 may be configured to indicate an acceptable level of sterilization after 12 minutes at 121° C., and may include the base element 16, the first adhesive layer 22, the wicking element 20, the film layer 26, the second adhesive layer 30, the paper layer 28, and the indicator chemical composition 14, in which the film layer 26 is formed from a cast polypropylene film having a thickness of about 2.2 mil, and the wicking element 20 is formed from a wicking paper having a basis weight of about 87.7 g/m$^2$ and a thickness of about 7.5 mil. The porosity of the wicking paper correlates with the basis weight and thickness of the wicking paper.

All patents referred to herein, are hereby incorporated herein by reference, whether or not specifically done so within the text of this disclosure.

In the present disclosure, the words "a" or "an" are to be taken to include both the singular and the plural. Conversely, any reference to plural items shall, where appropriate, include the singular.

From the foregoing it will be observed that numerous modifications and variations can be effectuated without departing from the true spirit and scope of the novel concepts of the present disclosure. It is to be understood that no limitation with respect to the specific embodiments illustrated is intended or should be inferred. The disclosure is intended to cover all such modifications as fall within the scope of the disclosure.

What is claimed is:

1. A sterilization indicator, comprising:
   a base element formed from a thermally conductive material having a length and a width, the base element having a recess formed therein extending along about a longitudinal centerline thereof, the recess formed within the base material less than the length and the width of the base material;
   a first adhesive layer disposed on the base element;
   an indicator chemical composition deposited in the recess;
   a wicking element positioned at least in part in contact with the indicator chemical composition and positioned at least in part within the recess, the wicking element extending less than the length and width of the base element, wherein the wicking element includes a first zone, a second zone, and a third zone, wherein the first zone has a generally constant width $W_{38}$ and the third zone has a generally constant width $W_{40}$, wherein $W_{38}$ is less than $W_{40}$, wherein the second zone is arranged between the first zone and the third zone and has a width that increases from $W_{38}$ to $W_{40}$, wherein a wicking rate across the first zone is greater than a wicking rate across the third zone, wherein the wicking element is arranged such that an end portion of the first zone is in contact with the indicator chemical composition;

a film layer positioned over the base element, the wicking element and the indicator chemical composition;

a paper layer disposed over the film layer;

a second adhesive layer disposed between the paper layer and the film layer, wherein the paper layer and the second adhesive layer include a window therein; and an acceptance marker;

wherein, the indicator is configured to indicate that an acceptable level of sterilization has occurred when the indicator chemical composition wicks along the wicking element to a location beyond the acceptance marker after a sterilization process.

2. The sterilization indicator of claim 1, wherein the indicator chemical composition contains a temperature and steam sensitive material.

3. The sterilization indicator of claim 1, wherein the indicator chemical composition contains a dye.

4. The sterilization indicator of claim 1, wherein the film layer is formed from a cast polypropylene having a thickness of 2.0 to 2.2 mils.

5. The sterilization indicator of claim 1, wherein the film layer is formed from a cast polypropylene having a thickness of 3.0 to 3.2 mils.

6. The sterilization indicator of claim 1, wherein the base element formed from an aluminum foil.

7. The sterilization indicator of claim 1, wherein the base element is formed from an aluminum foil having a thickness of 3 mils.

8. The sterilization indicator of claim 1, wherein the first adhesive layer is formed from an acrylic adhesive.

9. The sterilization indicator of claim 1, wherein the second adhesive layer is formed from an acrylic adhesive.

10. The sterilization indicator of claim 1, wherein the wicking element is formed from a wicking paper having a basis weight of 66 g/m² to 186 g/m².

11. The sterilization indicator of claim 1, wherein the wicking element is formed from a wicking paper having a thickness of 7.3 mil to 13.3 mil.

12. A sterilization indicator, comprising:
a base element formed from a thermally conductive material having a length and a width, the base element having a recess formed therein extending along about a longitudinal centerline thereof, the recess formed within the base material less than the length and the width of the base material;

a first adhesive layer disposed on the base element;

an indicator chemical composition deposited in the recess;

a wicking element positioned at least in part in contact with the indicator chemical composition and positioned at least in part within the recess, the wicking element extending less than the length and width of the base element, wherein the wicking element includes at least two zones comprising a first zone and a second zone, wherein the first zone has a thickness greater than a thickness of the second zone;

a film layer positioned over the base element, the wicking element and the indicator chemical composition;

a paper layer disposed over the film layer;

a second adhesive layer disposed between the paper layer and the film layer, wherein the paper layer and the second adhesive layer include a window therein; and an acceptance marker;

wherein, the indicator is configured to indicate that an acceptable level of sterilization has occurred when the indicator chemical composition wicks along the wicking element to a location beyond the acceptance marker after a sterilization process.

13. The sterilization indicator of claim 12, wherein the wicking element is formed from a layer of a wicking paper, wherein the first zone includes a second layer of a wicking paper.

14. A sterilization indicator, comprising:
a base element formed from a thermally conductive material having a length and a width, the base element having a recess formed therein extending along about a longitudinal centerline thereof, the recess formed within the base material less than the length and the width of the base material;

a first adhesive layer disposed on the base element;

an indicator chemical composition deposited in the recess;

a wicking element positioned at least in part in contact with the indicator chemical composition and positioned at least in part within the recess, the wicking element extending less than the length and width of the base element, wherein the wicking element includes at least two zones comprising a first zone and a second zone, wherein the first zone is formed from a first wicking paper and the second zone is formed from a second wicking paper, wherein a wicking rate of the first wicking paper is greater than a wicking rate of the second wicking paper;

a film layer positioned over the base element, the wicking element and the indicator chemical composition;

a paper layer disposed over the film layer;

a second adhesive layer disposed between the paper layer and the film layer, wherein the paper layer and the second adhesive layer include a window therein; and an acceptance marker;

wherein, the indicator is configured to indicate that an acceptable level of sterilization has occurred when the indicator chemical composition wicks along the wicking element to a location beyond the acceptance marker after a sterilization process.

15. A sterilization indicator, comprising:
a base element formed from a thermally conductive material having a length and a width, the base element having a recess formed therein extending along about a longitudinal centerline thereof, the recess formed within the base material less than the length and the width of the base material;

a first adhesive layer disposed on the base element;

an indicator chemical composition deposited in the recess;

a wicking element positioned at least in part in contact with the indicator chemical composition and positioned at least in part within the recess, the wicking element extending less than the length and width of the base element, wherein the wicking element includes a first zone, a second zone, and a third zone, wherein a width of the first zone is less than a width of the third zone, wherein the second zone is arranged between the first zone and the third zone and has a width that increases from the width of the first zone to the width of the third zone, wherein the wicking element is position such that an end portion of the first zone is in contact with the indicator chemical composition, wherein the base element has a length of 1.75 inches to 4 inches, and the wicking element has a length of 1.125 inches to 1.625 inches, wherein the first zone has a width of 0.125 inches to 0.375 inches and the third zone has a width of 0.175 inches to 0.425 inches, wherein the width of the first zone is 0.03 inches to 0.07 inches less than the width of the third zone, wherein a criteria for the sterilization process is selected from 12 minutes at 121° C., 15 minutes at 121° C., 20 minutes at 121° C., 30 minutes at 121° C., 4 minutes at 132° C., 3.5 minutes at 134° C., 4 minutes at 134° C., 5 minutes at 134° C., 7 minutes at 134° C., and 3 minutes at 135° C.;

a film layer positioned over the base element, the wicking element and the indicator chemical composition;

a paper layer disposed over the film layer;

a second adhesive layer disposed between the paper layer and the film layer, wherein the paper layer and the second adhesive layer include a window therein; and an acceptance marker;

wherein, the indicator is configured to indicate that an acceptable level of sterilization has occurred when the indicator chemical composition wicks along the wicking element to a location beyond the acceptance marker after a sterilization process.

16. The sterilization indicator of claim 15, wherein the indicator chemical composition contains a temperature and steam sensitive material, wherein the film layer is formed from a cast polypropylene having a thickness of 2.0 to 2.2 mils or a thickness of 3.0 to 3.2 mils, and wherein the wicking element is formed from a cotton wicking material having a basis weight of 186 $g/m^2$ and a thickness of 13.3 mil.

* * * * *